United States Patent [19]

Casado et al.

[11] Patent Number: 5,618,945

[45] Date of Patent: Apr. 8, 1997

[54] PROCESS FOR THE SULFINYLATION OF HETEROCYCLIC COMPOUNDS

[75] Inventors: Michel Casado, St. Symphorien D'Ozon; Pierre Le Roy; Virginie Pevfre, both of Lyons, all of France

[73] Assignee: Rhone-Poulenc Agrochimie, Lyon Cedex, France

[21] Appl. No.: 392,243

[22] Filed: Feb. 22, 1995

[30] Foreign Application Priority Data

Feb. 22, 1904 [FR] France ................... 94 02222

[51] Int. Cl.⁶ .............. C07D 233/84; C07D 233/68; C07D 231/14; A01N 43/50; A01N 43/36; A01N 43/56

[52] U.S. Cl. .............. 548/367.4; 548/323.5; 548/325.1; 548/550

[58] Field of Search ............ 548/325, 1, 367.4, 548/550

[56] References Cited

U.S. PATENT DOCUMENTS

| | | | |
|---|---|---|---|
| 4,966,901 | 10/1990 | Zoller et al. | 514/211 |
| 5,082,945 | 1/1992 | Wakselman et al. | 548/110 |
| 5,187,185 | 2/1993 | Outcalt et al. | 514/408 |
| 5,223,525 | 6/1993 | Wu et al. | 514/398 |
| 5,232,940 | 8/1993 | Hatton et al. | 514/407 |
| 5,283,337 | 2/1994 | Wakselman et al. | 546/279 |

FOREIGN PATENT DOCUMENTS

| | | | |
|---|---|---|---|
| 0295117 | 12/1988 | European Pat. Off. | 514/407 |
| 0346683 | 12/1989 | European Pat. Off. | 514/211 |
| 55-157570 | 12/1980 | Japan | 548/333.5 |
| 93/06089 | 4/1993 | WIPO | 514/211 |

OTHER PUBLICATIONS

O. Carmona et al, *Journal of Organic Chemistry*, vol. 45, No. 26, Dec. 19, 1980, pp. 5336–5339.

K. Andersen et al, *Journal of Organic Chemistry*, vol. 48, No. 25, Dec. 16, 1983, pp. 4803–4807.

*Primary Examiner*—Floyd D. Higel
*Attorney, Agent, or Firm*—Burns, Doane, Swecker & Mathis, L.L.P.

[57] ABSTRACT

The invention relates to a novel process for the sulfinylation of heterocyclic compounds, which comprises reacting:

a compound of the formula RS(O)X, in which R is a linear or branched alkyl group having from 1 to 4 carbon atoms, which is substituted with one or more identical or different halogen atoms and X is a halogen atom, the hydroxyl group or one of the salts thereof, a group —NR$_2$R$_3$, R$_2$ and R$_3$ being alkyl or haloalkyl groups of 1 to 4 carbon atoms, or an aryloxy or aralkoxy group, in which the aryl part preferably corresponds to a phenyl group, which is optionally substituted with one or more halogen atoms or alkyl or haloalkyl groups of 1 to 4 carbon atoms, with a heterocyclic compound Het chosen from the group consisting of pyrroles, pyrazoles, imidazoles, oxazoles, isoxazoles, thiazoles, isothiazoles and triazoles, all of these heterocycles Het optionally being substituted with one or more atoms or groups chosen from halogen, amine, alkylamine, dialkylamine, nitrile, aryl, and aryl substituted with one or more halogen atoms and/or one or more alkyl, haloalkyl or SF$_5$ groups.

43 Claims, No Drawings

PROCESS FOR THE SULFINYLATION OF HETEROCYCLIC COMPOUNDS

The present invention relates to a novel process for the sulfinylation of heterocyclic compounds.

The sulfinylation of heterocyclic compounds, that is to say the incorporation of a group RS(O)—, is conventionally performed by the action of a product of formula RSX (R and X being defined below) on the heterocyclic compound bearing a hydrogen atom on the carbon to be substituted. This reaction thus leads to the sulfenyl heterocyclic compound, which must be oxidized to give the desired sulfinyl compound. However, it is found that this oxidation step is often difficult. Furthermore, the compound RSX has been found, in certain cases, to be very toxic. This is the case, for example, of the compound $CF_3SCl$, thus making the manipulations very intricate. Another conventional process consists in proceeding via an intermediate disulfide compound, which is cleaved at the S—S bond by a compound RX, thereby giving the sulfenyl compound, which is then oxidized into the sulfinyl compound. This process avoids the use of compound RSX but does not avoid the subsequent oxidation step.

AIM OF THE INVENTION

The object of the present invention is thus to avoid the above two drawbacks (difficult oxidation and toxicity of the reactant) by proposing a process of direct sulfinylation by the action of RS(O)X on heterocyclic compounds without damaging the overall yield for the reaction and while at the same time reducing the number of reaction steps. A process has now been found which satisfies, in whole or in part, these objectives of ease of performance, of yield and of safety, this process constituting the subject of the present invention.

TECHNICAL CONTEXT AND PRIOR ART

Published European Patent Applications EP 0295 117, 0460940 and 0484165 give numerous examples of access to sulfinylated heterocyclic compounds. Two types of processes are thus apparent:

A first process group consists in producing the sulfenylated compound which must subsequently be oxidized in order to obtain the desired compound. Sulfenylated compounds are prepared by the direct action of a reactant RSX on the heterocyclic compound having a hydrogen atom at the position to be sulfenylated, or by the action of organomagnesium reagents or compounds R'I or R'Br (R' being an alkyl or haloalkyl group) on a thiocyanato heterocycle, or finally by reduction of disulfide compounds in the presence of compounds R'I. These various processes are described in published European Patent Application EP A 0295117 (cf. processes b, d1, d2 and d3 on pages 11–12). Another process using disulfide compounds is described in European Patent EP B1 0374061.

A second group consists in reacting a sulfinylated compound with a specific compound such that the product of this reaction will form the sulfinylated heterocyclic compound by cyclization. Reference will again be made to published European Application EP A 0295117 (cf. processes a and c on page 11 ) for the details of these processes.

Moreover, in the aromatic and non-heterocyclic series, references based on direct aromatic (phenyl ring) sulfinylation are known. For example, *Bull. Chem. Soc. Jpn.* 46, (1973) 3615 describes the sulfinylation reaction of methoxybenzene by p-methylphenylsulfinyl chloride in the presence of $AlCl_3$ catalyst. Another reaction of this type is described in *Zh Org Khim*, 17 (9) (1981) 1800. In this reaction, a Grignard reagent, namely para-methylbenzenemagnesium bromide, is placed together with naphthylsulfinyl chloride.

DESCRIPTION OF THE PRESENT INVENTION

The subject of the invention is a novel process for the sulfinylation of heterocyclic compounds, which comprises reacting:

a derivative of formula RS(O)X, in which R is a linear or branched alkyl group having from 1 to 4 carbon atoms, which is substituted with one or more identical or different halogen atoms and X is a halogen atom, the hydroxyl group or one of the salts thereof, a radical of the formula —$NR_2R_3$, $R_2$ and $R_3$ being alkyl or haloalkyl groups of 1 to 4 carbon atoms, or an aryloxy or aralkoxy group (in which the aryl part preferably corresponds to a phenyl group, that is, when X is aryloxy or aralkoxy, it is preferably a phenoxy or benzyloxy radical), either of which is unsubstituted or substituted with one or more halogen atoms or alkyl or haloalkyl groups of 1 to 4 carbon atoms, with a heterocyclic compound Het chosen from the group consisting of pyrroles, pyrazoles, imidazoles, oxazoles, isoxazoles, thiazoles, isothiazoles and triazoles, all of these heterocycles Het optionally being substituted with one or more atoms or groups chosen from halogen, amine unsubstituted or substituted by one or two alkyl groups of 1 to 4 carbon atoms, nitrile, aryl (especially phenyl), aryl (especially phenyl) substituted with one or more halogen atoms and/or one or more alkyl (preferably $C_1$–$C_4$ alkyl), haloalkyl (preferably $C_{1-4}$ haloalkyl, especially $CF_3$) or $SF_5$ groups.

When X is a salt of a hydroxyl group, it is preferably an alkali metal or alkaline-earth metal salt such as a sodium, potassium, magnesium or calcium salt.

A preferred process comprises choosing the heterocycle Het from the group consisting of pyrroles, pyrazoles and imidazoles and in this case a compound C, chosen from the group consisting of the tosylates, hydrochlorides and mesylates of a primary, secondary or tertiary amine, preferably of dimethylamine, of pyridine, of trimethylamine, of diethylamine or of isopropylamine, or gaseous hydrogen chloride, optionally in the presence of an approximately equimolar amount of para-toluenesulfonic acid, may be added to complete the reaction.

A reactant chosen from the group consisting of phosgene ($COCl_2$), chloroformates, $PCl_5$ and $SOCl_2$ may optionally be used to perform the above-mentioned reactions.

A heterocycle substituted with an amino group is advantageously chosen. This group then reacts with RS(O)X to give a sulfinamide compound, which subsequently rearranges to give a heterocyclic compound having an amino group borne by one carbon atom and a sulfinyl group RS(O) on the vicinal carbon.

According to a specific embodiment of the invention, the compound $CF_3S(O)X$ is used in which X is a chlorine atom. It is known that, in this case, the compound $CF_3S(O)Cl$ is less toxic than the compound $CF_3SCl$ used previously, which constitutes one of the advantages of the present invention. In addition to this, the subsequent oxidation step is also avoided, as has already been indicated. Furthermore, $CF_3SCl$ is a gaseous compound at room temperature, whereas $CF_3S(O)Cl$ is liquid, which makes the manipulations easier.

According to a second specific embodiment of the invention, the compound $CF_3S(O)X$ is used in which X is the $N(CH_3)_2$ or $N(C_2H_5)_2$ group.

According to a third specific embodiment of the invention, the compound $CF_3S(O)X$ is used in which X is the hydroxyl OH or ONa group, and in this case the reaction is performed in the presence of phosgene ($COCl_2$) or $SOCl_2$.

The process, and the preferred embodiments thereof, is particularly suitable when the heterocycle Het is a compound of formula A or B below:

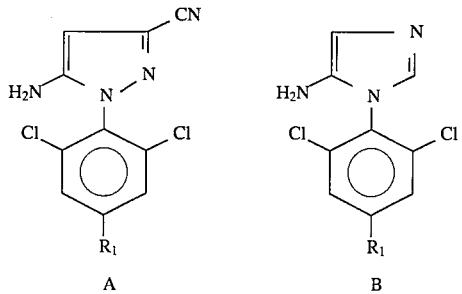

in which $R_1$ represents a halogen atom, preferably fluorine, or an alkyl or haloalkyl group, preferably $C_{1-4}$ alkyl or haloalkyl, most preferably $CF_3$, or an $SF_5$ group. The process provides the corresponding sulfinylated heterocycles which have valuable properties, for example, insecticidal activity.

The invention also relates to a process for the production of 4-sulfinylpyrazoles of the formula:

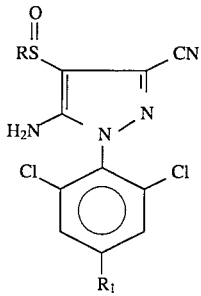

in which R is a linear or branched alkyl group having from one to four carbon atoms, which is substituted with one or more identical or different halogen atoms, and $R_1$ represents a halogen atom, preferably fluorine, or an alkyl or haloalkyl group, preferably $C_1$–$C_4$ alkyl or haloalkyl, especially $CF_3$, or an $SF_5$ group, starting with compounds of the formula:

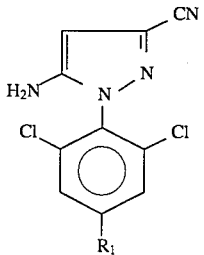

by the action of a reactant of the formula RS(O)X, in which R is a linear or branched alkyl group having from one to four carbon atoms, which is substituted with one or more identical or different halogen atoms and X is a halogen atom, a hydroxyl group or one of the salts thereof, or a radical of the formula —$NR_2R_3$, $R_2$ and $R_3$ being alkyl or haloalkyl groups of 1 to 4 carbon atoms, or X is an aryloxy or aralkoxy group, preferably a phenoxy or benzyloxy group, either of which is optionally substituted with one or more halogen atoms or alkyl or haloalkyl groups of 1 to 4 carbon atoms. The process is performed with a molar excess of reactant RS(O)X relative to the 4-H pyrazole compound above. This excess is of the order of 10 to 50%, preferably of 20 to 30%.

A compound C chosen from the group consisting of the tosylates, hydrochlorides or mesylates of any primary, secondary or tertiary amine, preferably of dimethylamine, of pyridine, of trimethylamine, of diethylamine or of isopropylamine, is advantageously used in order to complete the above reaction. This compound C may also be gaseous hydrogen chloride, which is optionally in the presence of an approximately equimolar amount of para-toluenesulfonic acid. The molar ratio between the compound C and the heterocyclic compound is advantageously between 0.5 and 2, and preferably between 1 and 2. Moreover, the reaction is performed in an organic medium, preferably in a solvent chosen from the group comprising toluene, 1,2-dichloroethane and dichloromethane. The reaction temperature is between 0° and 100° C., preferably between 3° and 60° C. and even more preferably between 30° and 55° C.

A reactant chosen from the group consisting of phosgene ($COCl_2$), chloroformates, $PCl_5$ and $SOCl_2$ may optionally be used to perform the above-mentioned reactions.

The process thus provides the desired 4-sulfinylpyrazoles, which are valuable insecticides.

The above process for the sulfinylation of pyrazoles is even more advantageously useful for producing the 4-sulfinylpyrazoles of the formulae:

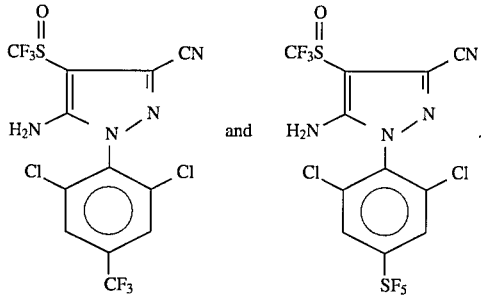

Either $CF_3S(O)Cl$, $CF_3S(O)N(CH_3)_2$ or $CF_3S(O)N(C_2H_5)_2$, or $CF_3S(O)OH$ or $CF_3S(O)ONa$ with phosgene or $SOCl_2$ or $ClCO_2C_2H_5$, according to the described process and embodiments thereof, is then reacted with a 4-H pyrazole compound having the formula:

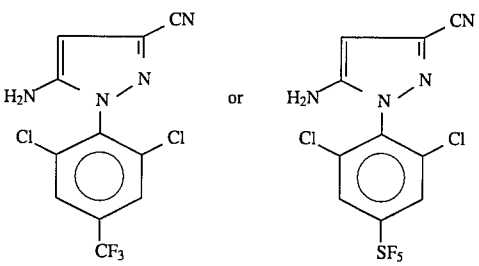

The invention also relates to intermediate sulfinamide compounds of the formula $RS(O)NH$—$Het_1$, in which $Het_1$—$NH_2$ is an amino-substituted heterocycle chosen from the group consisting of pyrroles, pyrazoles, imidazoles, oxazoles, isoxazoles, thiazoles, isothiazoles and triazoles, all of these heterocycles $Het_1$—$NH_2$ optionally being substituted with one or more atoms or groups chosen from halogen, amine unsubstituted or substituted by one or two alkyl groups of 1 to 4 carbon atoms, nitrile, aryl (especially phenyl), and aryl (especially phenyl) substituted with one or more halogen atoms and/or one or more alkyl (preferably $C_1$-$C_4$ alkyl), haloalkyl (preferably $C_1$-$C_4$ haloalkyl, especially $CF_3$) and $SF_5$ groups.

The compounds RS(O)NH—$Het_1$, where $Het_1$—$NH_2$ is an amino-substituted pyrazole heterocycle which is optionally substituted with one or more atoms or groups chosen from halogen, amine unsubstituted or substituted by one or two alkyl groups of 1 to 4 carbon atoms, nitrile, aryl (preferably phenyl), and aryl (preferably phenyl) substituted with one or more halogen atoms and/or one or more alkyl (preferably $C_1$-$C_4$ alkyl), haloalkyl (preferably $C_1$-$C_4$ haloalkyl, especially $CF_3$) or $SF_5$ groups and where the sulfinamide group is in position 5 on this heterocycle, more advantageously form part of the present invention.

Even more advantageously, the invention relates to the compounds 5-(N-trifluoromethylsulfinyl)amino-3-cyano-1-[2,6-dichloro-4$CF_3$-phenyl]-4-H-Pyrazole and 5-(N-trifluoromethylsulfinyl)amino-3-cyano-1-[2,6-dichloro-4-$SF_5$-phenyl]-4-H-pyrazole.

EXAMPLES

The examples which follow, given with no limitation being implied, illustrate the invention and show how it may be implemented, Example 1

Sulfinylation using $CF_3S(O)Cl$: synthesis of 5-amino-3-cyano-1-(2,6-dichloro-4-trifluoromethylphenyl)-4-trifluoromethylsulfinylpyrazole.

8.06 g (25 mmol) of 5-amino-3-cyano-1-(2,6-dichloro-4-trifluoromethylphenyl)pyrazole and 8.15 g (38 mmol) of dimethylamine tosylate are suspended in 50 ml of toluene.

Trifluoromethylsulfinyl chloride (5 g, i.e. 32 mmol) is rapidly added to this mixture. The reaction medium is then heated to 50° C. After reaction for 8 hours at this temperature, the reaction is flushed with a stream of argon. The reaction medium is then cooled to 20° C. 20 ml of water are added thereto and the precipitate is then filtered off and washed with water, then with toluene.

The product obtained is dried in the heat under vacuum. 9.77 g (i.e. a yield of 88%) of 5-amino-3-cyano-1-(2,6-dichloro-4-trifluoromethylphenyl)-4-trifluoromethylsulfinylpyrazole are thus obtained, in a purity of more than 95% (determined by HPLC).

The physical and spectral characteristics of the compound obtained are as follows:

Melting point=196°–198° C.

NMR analysis: $^1H$ proton NMR, $CDCl_3$, TMS: 5.1 ppm (s, 2H), 7.8 ppm (s, 2H). $^{13}C$ carbon NMR, acetone-$d_6$, TMS: Phenyl group: $C_1$: 135.4 ppm, $C_2$: 137.5 ppm, $C_3$: 127.6 ppm, $C_4$: 135.5 ppm, $C(CF_3)$: 123 ppm. Pyrazole group: $C_3$: 126.7 ppm, $C_4$: 94.6 ppm, $C_5$: 152.3 ppm, C(CN): 111.7 ppm, $C(CF_3)$: 126.3 ppm. Mass analysis, EI+: M=436 ($^{35}Cl$).

Example 2

Sulfinylation using $CF_3S(O)Cl$: synthesis of 5-amino-3-cyano-1-(2,6-dichloro-4-trifluoromethylphenyl)-4-trifluoromethylsulfinylpyrazole.

0.81 g (2.5 mmol) of 5-amino-3-cyano-1-(2,6-dichloro-4-trifluoromethylphenyl)pyrazole and 0.29 g (2.5 mmol) of dry pyridine hydrochloride are dissolved in 5 ml of 1,2-dichloroethane.

Trifluoromethylsulfinyl chloride (0.5 g, i.e. 3.2 mmol) is added to this mixture. The reaction medium is then heated at 50° C. for 10 hours. The process is then performed as in the above example.

The yield assayed as 5-amino-3-cyano-1-(2,6-dichloro-4-trifluoromethylphenyl)-4-trifluoromethylsulfinylpyrazole is thus 74%.

Example 3

Sulfinylation using $CF_3S(O)NMe_2$: synthesis of 5-amino-3-cyano-1-(2,6-dichloro-4-trifluoromethylphenyl)-4-trifluoromethylsulfinylpyrazole.

0.81 g (2.5 mmol) of 5-amino-3-cyano-1-(2,6-dichloro-4-trifluoromethylphenyl)pyrazole and 0.55 g (2.5 mmol) of dry para-toluenesulfonic acid are suspended in 5 ml of toluene. N,N-dimethyltrifluoromethylsulfinylamine (0.53 g, i.e. 3.2 mmol) is then added to the medium, followed by a solution of HCl in toluene (i.e. 2.5 mmol). This medium is heated for 8 hours at 50° C. The process is then performed as in Example 1.

The yield assayed as 5-amino-3-cyano-1-(2,6-dichloro-4-trifluoromethylphenyl)-4-trifluoromethylsulfinylpyrazole is thus 72%.

Example 4

Synthesis of 5-(N-trifluoromethylsulfinyl) amino-3-cyano-1-(2,6-dichloro-4-trifluoromethylphenyl)pyrazole.

The sulfinamide pyrazole, which is included within the present invention, may be prepared and isolated according to the following conditions:

3.23 g (10 mmol) of 5-amino-3-cyano-1-(2,6-dichloro-4-trifluoromethylphenyl)pyrazole and 3.25 g (15 mmol) of dimethylamine tosylate are suspended in 20 ml of toluene. The temperature is brought to 5° C. Trifluoromethylsulfinyl chloride (2 g, i.e. 13 mmol) is added rapidly. A solution of dimethylamine (5 mmol) in toluene is then added.

The reaction is left stirring for 30 minutes at 5° C. 50 ml of methyl tert-butyl ether are then added. The precipitate formed is eliminated by filtration and then rinsed. The filtrate is recovered and washed by extraction using 2×10 ml of ice-water. The organic phase is concentrated. The residue obtained is crystallized from toluene.

1.75 g of 5-(N-trifluoromethylsulfinyl)amino-3-cyano-1-(2,6-dichloro-4-trifluoromethylphenyl)pyrazole are thus obtained.

The physical and spectral characteristics of the compound obtained are as follows:

Melting point=123°–124° C.

NMR analysis: $^1H$ proton NMR, acetone-$d_6$, HMDS: 7.06 ppm (s, 1H), 8.06 ppm (s, 2H). $^{13}C$ carbon NMR, acetone-$d_6$, TMS: Phenyl group: $C_1$: 136.2 ppm, $C_2$: 137 ppm, $C_3$: 127.4 ppm, $C_4$: 135.2 ppm, $C(CF_3)$: 123.3 ppm. Pyrazole group: $C_3$: 128.5 ppm, $C_4$: 105.7 ppm, $C_5$: 140.7 ppm, C(CN): 113.5 ppm, $C(CF_3)$: 124.5 ppm.

Example 5

Synthesis of 5-amino-3-cyano-1-(2,6-dichloro-4-trifluoromethylphenyl)-4-trifluoromethylsulfinylpyrazole by rearrangement of the sulfinamide pyrazole of Example 4.

0.109 g (0.25 mmol) of the sulfinamide pyrazole obtained in the above example and 0.075 g (0.33 mmol) of dimethylamine tosylate are suspended in toluene. A solution of hydrochloric acid in toluene (equivalent to 0.25 mmol of HCl) is added. The reaction medium is heated for 10 hours at 50° C.

The yield assayed as 5-amino-3-cyano-1-(2,6-dichloro-4-trifluoromethylphenyl)-4-trifluoromethylsulfinylpyrazole is 80%.

Example 6

Sulfinylation using $CF_3S(O)ONa$: synthesis of 5-amino-3-cyano-1-(2,6-dichloro-4-trifluoromethylphenyl)-4-trifluoromethylsulfinylpyrazole.

0.81 g (2.5 mmol) of 5-amino-3-cyano-1-(2,6-dichloro-4-trifluoromethylphenyl)pyrazole, 0.815 g (3.8 mmol) of dimethylamine tosylate and 0.51 g (3.25 mmol) of the sodium salt of trifluoromethanesulfinic acid are suspended in 5 ml of toluene. This mixture is cooled to 5° C. and $SOCl_2$ is added, followed by stirring for approximately 1 hour at room temperature. The reaction medium is then heated at 50° C. for 8 hours. The process is then performed as in Example 1.

The yield assayed as 5-amino-3-cyano-1-(2,6-dichloro-4-trifluoromethylphenyl)-4-trifluoromethylsulfinylpyrazole is 66%.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A process for the sulfinylation of a heterocyclic compound comprising reacting a compound of the formula RS(O)X, wherein R is straight or branched alkyl having from 1 to 4 carbon atoms, which is substituted with one or more identical or different halogen atoms, and X is a halogen atom, a hydroxyl group or salt thereof, a radical of the formula —$NR_2R_3$ wherein $R_2$ and $R_3$ are alkyl or haloalkyl having from 1 to 4 carbon atoms, or an aryloxy or aralkoxy radical, the aryl portion of which is unsubstituted or is substituted with one or more halogen atoms or alkyl or haloalkyl radicals having from 1 to 4 carbon atoms, with a heterocyclic compound Het selected from the group consisting of pyrroles, pyrazoles, imidazoles, oxazoles, isoxazoles, thiazoles, isothiazoles and triazoles, said heterocyclic compound Het being unsubstituted or being substituted with one or more members selected from the group consisting of halogen, amino which is unsubstituted or is substituted with one or two alkyl having from 1 to 4 carbon atoms, nitrile, aryl, and aryl having one or more substituents selected from the group consisting of halogen, alkyl, haloalkyl and $SF_5$, in the presence of (a) a compound selected from the group consisting of the tosylates, hydrochlorides and mesylates of primary, secondary and tertiary amines, or (b) hydrochloric acid.

2. The process according to claim 1, wherein Het is selected from the group consisting of pyrroles, pyrazoles and imidazoles.

3. The process according to claim 2, wherein (a) is a tosylate, hydrochloride or mesylate of dimethylamine, pyridine, trimethylamine, diethylamine or isopropylamine.

4. The process according to claim 1, wherein the reaction is carried out in the presence of phosgene, a chloroformate, $PCl_5$ or $SOCl_2$.

5. The process according to claim 2, wherein the reaction is carried out in the presence of phosgene, a chloroformate, $PCl_5$ or $SOCl_2$.

6. The process according to claim 3, wherein the reaction is carried out in the presence of phosgene, a chloroformate, $PCl_5$ or $SOCl_2$.

7. The process according to claim 2, wherein the reaction is carried out in the presence of (b) hydrochloric acid and further in the presence of para-toluenesulfonic acid.

8. A process for the sulfinylation of a heterocyclic compound comprising reacting a compound of the formula RS(O)X, wherein R is straight or branched alkyl having from 1 to 4 carbon atoms, which is substituted with one or more identical or different halogen atoms, and X is a halogen atom, a hydroxyl group or salt thereof, a radical of the formula —$NR_2R_3$ wherein $R_2$ and $R_3$ are alkyl or haloalkyl having from 1 to 4 carbon atoms, or an aryloxy or aralkoxy radical, the aryl portion of which is unsubstituted or is substituted with one or more halogen atoms or alkyl or haloalkyl radicals having from 1 to 4 carbon atoms, with a heterocyclic compound Het selected from the group consisting of pyrroles, pyrazoles, imidazoles, oxazoles, isoxazoles, thiazoles, isothiazoles and triazoles, said heterocyclic compound Het being substituted with amino and further being unsubstituted or substituted with one or more members selected from the group consisting of halogen, amino which is unsubstituted or is substituted with one or two alkyl having from 1 to 4 carbon atoms, nitrile, aryl, and aryl having one or more substituents selected from the group consisting of halogen, alkyl, haloalkyl and $SF_5$, wherein said Het reacts with the compound RS(O)X to afford a sulfinamide, and wherein the resultant sulfinamide is subjected to rearrangement to afford a heterocyclic compound having an amino substituent borne by one carbon atom and a sulfinyl group RS(O) on the vicinal carbon.

9. The process according to claim 8, wherein Het is selected from the group consisting of pyrroles, pyrazoles and imidazoles and wherein the reaction is carried out in the presence of (a) a compound selected from the group consisting of the tosylates, hydrochlorides and mesylates of primary, secondary and tertiary amines, or (b) hydrochloric acid.

10. The process according to claim 9, wherein (a) is a tosylate, hydrochloride or mesylate of dimethylamine, pyridine, trimethylamine, diethylamine or isoporpylamine.

11. The process according to claim 8, wherein the reaction is carried out in the presence of phosgene, a chloroformate, $PCl_5$ or $SOCl_2$.

12. The process according to claim 9, wherein the reaction is carried out in the presence of phosgene, a chloroformate, $PCl_5$ or $SOCl_2$.

13. The process according to claim 10, wherein the reaction is carried out in the presence of phosgene, a chloroformate, $PCl_5$ or $SOCl_2$.

14. The process according to claim 1, wherein R is —$CF_3$ and X is Cl.

15. The process according to claim 2, wherein R is —$CF_3$ and X is Cl.

16. The process according to claim 4, wherein R is —$CF_3$ and X is Cl.

17. The process according to claim 8, wherein R is —$CF_3$ and X is Cl.

18. The process according to claim 1, wherein R is —$CF_3$ and X is —$N(CH_3)_2$ or —$N(C_2H_5)_2$.

19. The process according to claim 2, wherein R is —$CF_3$ and X is —$N(CH_3)_2$ or —$N(C_2H_5)_2$.

20. The process according to claim 4, wherein R is —$CF_3$ and X is —$N(CH_3)_2$ or $N(C_2H_5)_2$.

21. The process according to claim 8, wherein R is —CF$_3$ and X is —N(CH$_3$)$_2$ or —N(C$_2$H$_5$)$_2$.

22. The process according to claim 4, wherein R is —CF$_3$ and X is —OH or O$^-$Na$^+$ and wherein the reaction is carried out in the presence of phosgene or SOCl$_2$.

23. The process according to claim 11, wherein R is —CF$_3$ and X is —OH or O$^-$Na$^+$ and wherein the reaction is carried out in the presence of phosgene or SOCl$_2$.

24. The process according to claim 1, wherein Het is a compound of the formula

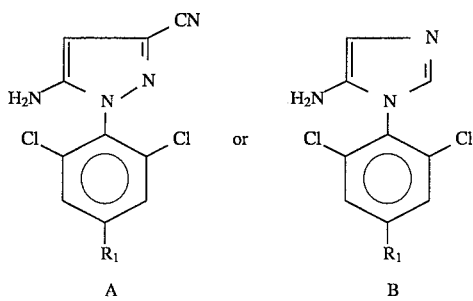

wherein R$_1$ is halogen, alkyl, haloalkyl or SF$_5$.

25. The process according to claim 24, wherein R$_1$ is F, CF$_3$ or SF$_5$.

26. The process according to claim 8, wherein Het is a compound of the formula

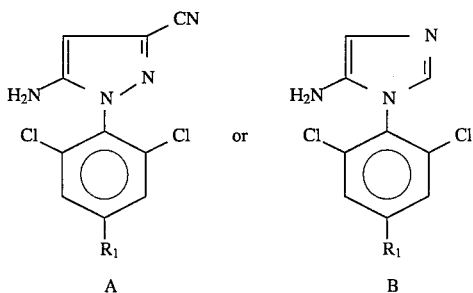

wherein R$_1$ is halogen, alkyl, haloalkyl or —SF$_5$.

27. The process according to claim 26, wherein R$_1$ is F, CF$_3$ or SF$_5$.

28. A process for the preparation of a compound of the formula

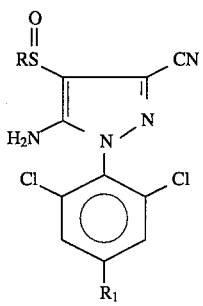

wherein R is straight or branched alkyl having one to four carbon atoms, which is substituted with one or more identical or different halogen atoms, and R$_1$ is halogen, alkyl, haloalkyl or SF$_5$, said process comprising reacting a compound of the formula

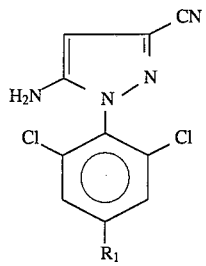

wherein R$_1$ is defined as above, with a compound of the formula RS(O)X wherein R is straight or branched alkyl having from 1 to 4 carbon atoms which is substituted with one or more identical or different halogen atoms, and X is a halogen atom, a hydroxyl group or salt thereof, or a radical of the formula —NR$_2$R$_3$ wherein R$_2$ and R$_3$ are alkyl or haloalkyl having from 1 to 4 carbon atoms, or X is an aryloxy or aralkoxy radical, the aryl portion of which is unsubstituted or is substituted with one or more halogen atoms or alkyl or haloalkyl radicals having 1 to 4 carbon atoms.

29. The process according to claim 28, wherein R$_1$ is F, CF$_3$ or SF$_5$.

30. The process according to claim 28, wherein X is halogen, hydroxyl or an alkali metal or alkaline-earth metal salt thereof, a —NR$_2$R$_3$ radical wherein R$_2$ and R$_3$ are alkyl or haloalkyl having 1 to 4 carbon atoms, or a phenoxy or benzyloxy radical, the phenyl portion of which is unsubstituted or substituted with one or more halogen atoms or alkyl or haloalkyl radicals having 1 to 4 carbon atoms.

31. The process according to claim 9, wherein the reaction is carried out in the presence of (b) hydrochloric acid and further in the presence of para-toluenesulfonic acid.

32. The process according to claim 28, wherein the reaction is carried out in the presence of (a) a compound selected from the group consisting of the tosylates, hydrochlorides and mesylates of primary, secondary and tertiary amines, or (b) hydrochloric acid.

33. The process according to claim 32, wherein the reaction is carried out in the presence of (b) hydrochloric acid and further in the presence of para-toluenesulfonic acid.

34. A process for the sulfinylation of a heterocyclic compound comprising reacting a compound of the formula RS(O)X, wherein R is straight or branched alkyl having from 1 to 4 carbon atoms, which is substituted with one or more identical or different halogen atoms, and X is a halogen atom, a hydroxyl group or salt thereof, a radical of the formula —NR$_2$R$_3$ wherein R$_2$ and R$_3$ are alkyl or haloalkyl having from 1 to 4 carbon atoms, or an aryloxy or aralkoxy radical, the aryl portion of which is unsubstituted or is substituted with one or more halogen atoms or alkyl or haloalkyl radicals having from 1 to 4 carbon atoms, with a heterocyclic compound Het selected from the group consisting of pyrazoles and imidazoles, said heterocyclic compound Het being unsubstituted or being substituted with one or more members selected from the group consisting of halogen, amino which is unsubstituted or is substituted with one or two alkyl having from 1 to 4 carbon atoms, nitrile, aryl, and aryl having one or more substituents selected from the group consisting of halogen, alkyl, haloalkyl and SF$_5$.

35. The process according to claim 32, wherein (a) is a tosylate, hydrochloride or mesylate of dimethylamine, pyridine, trimethylamine, diethylamine or isopropylamine.

36. The process according to claim 28, wherein the reaction is carried out in the presence of phosgene, a chloroformate, PCl$_5$ or SOCl$_2$.

37. The process according to claim 28 for the preparation of a compound

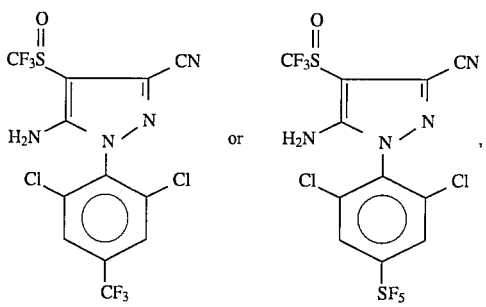

said process comprising reacting the corresponding compound of the formula

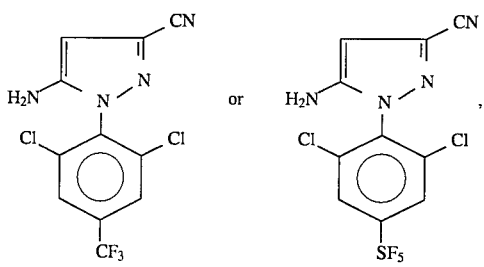

respectively, with:

(a) $CF_3S(O)Cl$, $CF_3S(O)N(CH_3)_2$ or $CF_3S(O)N(C_2H_5)_2$; or (b) $CF_3S(O)OH$ or $CF_3S(O)O^-Na^+$, in the presence of phosgene or $SOCl_2$ or $ClCO_2C_2H_5$.

38. A compound of the formula

wherein R is straight or branched alkyl having from 1 to 4 carbon atoms, which is substituted with one or more identical or different halogen atoms and NH—$Het_1$ is derived from a heterocycle $Het_1$—$NH_2$ which is selected from the group consisting of pyrroles, pyrazoles, imidazoles, oxazoles, isoxazoles, thiazoles, isothiazoles and triazoles, said heterocycle $Het_1$—$NH_2$ being substituted with a $NH_2$ group and optionally being further substituted with one or more members selected from the group consisting of halogen, amino which is unsubstituted or is substituted with one or two alkyl having from 1 to 4 carbon atoms, nitrile, aryl and aryl having one or more substituents selected from the group consisting of halogen, alkyl, haloalkyl and $SF_5$.

39. The compound according to claim 38, wherein $Het_1$—$NH_2$ is an amino-substituted pyrazole, which is optionally further substituted with one or more members selected from the group consisting of halogen, amino which is unsubstituted or is substituted with one or two alkyl having from 1 to 4 carbon atoms, nitrile, aryl, and aryl having one or more substituents selected from the group consisting of halogen, alkyl, haloalkyl and $SF_5$, and wherein the sulfinamide group is located in the 5-position of the pyrazole ring.

40. The compound according to claim 39, wherein said amino-substituted pyrazole is further substituted with one or more members selected from the group consisting of nitrile and phenyl having one or more substituents selected from the group consisting of halogen, alkyl, haloalkyl and $SF_5$.

41. The compound according to claim 40, wherein said amino-substituted pyrazole is substituted in the 1-position by phenyl, said phenyl having chloro substituents in the 2- and 6-positions and having a substituent in the 4-position selected from F, $CF_3$ and $SF_5$.

42. The compound according to claim 41, which is 5-(N-trifluoromethylsulfinyl)amino-3-cyano-1-[2,6-dichloro-4-$CF_3$-phenyl]-4H -pyrazole.

43. The compound according to claim 41, which is 5-(N-trifluoromethylsulfinyl)amino-3-cyano-1-[2,6-dichloro-4-$SF_5$-phenyl]-4H-pyrazole.

* * * * *